United States Patent [19]

Savinell et al.

[11] Patent Number: 4,689,994

[45] Date of Patent: Sep. 1, 1987

[54] DELIVERY SYSTEM FOR A REMOTE SENSOR

[75] Inventors: Alan Savinell, Penn Hills Twp., Allegheny County; Jeffrey E. Hydeman, Monroeville, both of Pa.

[73] Assignee: Westinghouse Electric Corp., Pittsburgh, Pa.

[21] Appl. No.: 670,421

[22] Filed: Nov. 9, 1984

[51] Int. Cl.$^4$ ............................................. G01N 29/00
[52] U.S. Cl. ........................................ 73/634; 73/152;
324/333; 324/366; 376/249; 376/252
[58] Field of Search .................. 73/634; 324/333, 346,
324/366; 376/249, 252, 248

[56] References Cited

U.S. PATENT DOCUMENTS

| | | | |
|---|---|---|---|
| 3,508,439 | 4/1970 | Alger | 73/152 |
| 3,824,843 | 7/1974 | Gebeshuber et al. | |
| 3,831,443 | 8/1974 | Planche et al. | 73/152 |
| 3,943,756 | 3/1976 | Aubert et al. | 73/634 |
| 4,117,733 | 10/1978 | Gugel | 73/634 |
| 4,255,972 | 3/1981 | Dijkstra | 73/634 |
| 4,302,286 | 11/1981 | Lefebvre et al. | 73/634 |
| 4,394,345 | 7/1983 | De Briere et al. | 376/249 |
| 4,432,271 | 2/1984 | Wentzell | 376/249 |
| 4,474,064 | 10/1984 | Naruse et al. | 376/252 |
| 4,597,294 | 7/1986 | Brill, III et al. | 376/252 |

FOREIGN PATENT DOCUMENTS

| | | |
|---|---|---|
| 098188 | 1/1984 | European Pat. Off. |
| 2153397 | 4/1974 | Fed. Rep. of Germany |
| 2902105 | 7/1979 | Fed. Rep. of Germany |
| 57-53657 | 3/1982 | Japan |

*Primary Examiner*—Howard A. Birmiel

[57] ABSTRACT

A mechanical delivery system for remotely positioning an ultrasonic sensor in mating engagement with a component to be inspected has an elongated support which can be manipulated at a first end from a remote location. A second end has an arm for carrying the sensor. A pin connects the arm to a housing which has an opening therein. A pinion gear is connected to the arm and a mating rack gear is connected to an actuator rod for moving the arm between a first position parallel to and within the housing and a second position wherein that portion of the arm carrying the sensor extends laterally of the housing through the housing's opening. The sensor is mounted on the arm such that it is permitted limited rotation about an axis perpendicular to the arm and limited rocking about a point on that axis thereby enabling the sensor to engage the component as a result of manipulation of the first end of the elongated support despite mispositioning of the second end of the support relative to the component.

44 Claims, 7 Drawing Figures

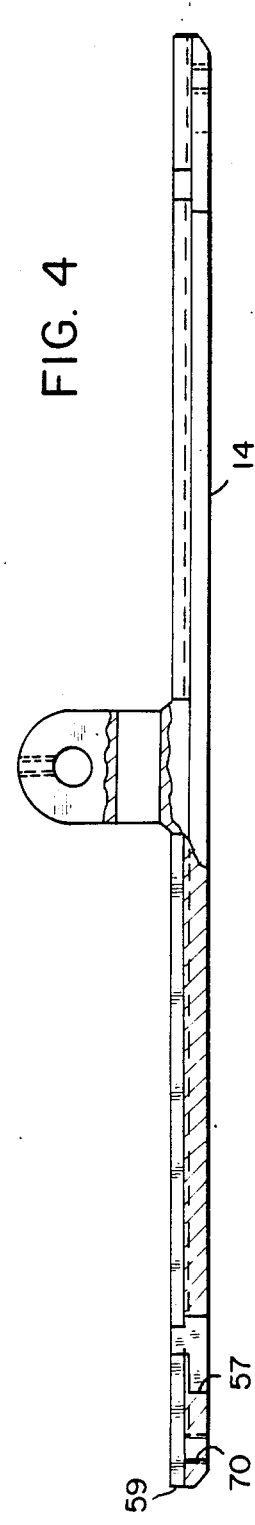
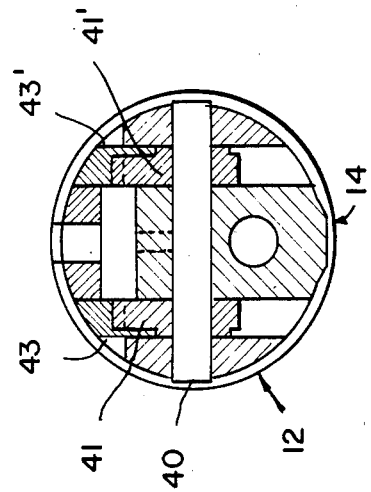
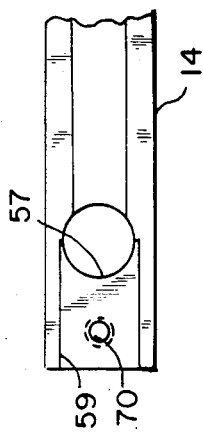
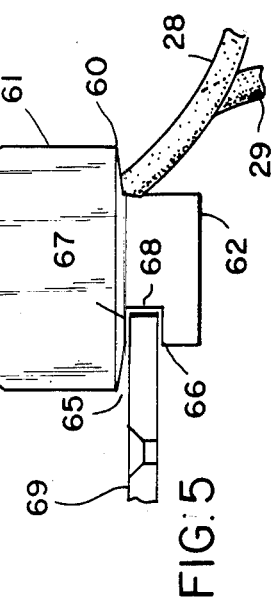

DELIVERY SYSTEM FOR A REMOTE SENSOR

BACKGROUND OF THE INVENTION

The present invention is related generally to remotely controllable sensors and more specifically to a mechanical delivery system for remotely positioning a contact-type ultrasonic sensor for inspecting components within a nuclear reactor.

The use of contact-type ultrasonic sensors is well-known for the inspection of mechanical components. It is also well-known to use remotely controllable delivery systems for positioning the ultrasonic sensor when manual positioning is not possible, i.e., because of space limitations, hostile environments, etc. However, certain environments, such as inside a nuclear reactor, present unique problems.

Typically, inspection of components within a nuclear reactor is necessary to gather data on operational performance, detect failures, comply with regulations or the like. Inspections typically occur during a scheduled outage for refueling or routine maintenance. Such outages are kept at minimal length for economic reasons. Thus, because of the short duration of the outage, it is necessary to perform a large number of complex inspections in a very short time.

In addition to the time constraints, the inspections must be performed from a platform above the nuclear reactor such that distances of thirty or even forty feet are not uncommon between the operator and the device being inspected. Further, the component to be inspected may have a notch or recess into which the ultrasonic sensor must be positioned. Thus, a specific orientation between the sensor and the component to be inspected must be achieved before the sensor can be inserted into the notch or recess. Attempts at inserting the sensor before the proper orientation is achieved may result in damage to the sensor. Damage to the sensors may also occur if the sensors collide with obstacles on the way to or from the component to be inspected.

Considering the complexity of a nuclear reactor, the large number of inspections which must be made in a short time, and the difficulty of the "blind38 positioning of a fragile sensor from a position forty feet away from the operator in a radioactive underwater environment, it is clear that the development of mechanical systems for remotely positioning the sensors presents a wide variety of challenges to the design engineer.

SUMMARY OF THE INVENTION

The present invention provides a mechanical delivery system and method for remotely positioning a portion of a contact-type sensor for mating engagement with a predetermined portion of a component to be inspected. The system includes elongated support means having a first end which can be manipulated from a remote location and a second end, and a sensor having a portion adapted for mating engagement with the predetermined portion of the component to be inspected. In accordance with one aspect of the present invention, the sensor is mounted to the elongated support means at the second end such that the sensor is permitted limited movement with respect to the second end. That limited movement allows the sensor portion to be placed in mating engagement with the predetermined portion of the component as a result of manipulation of the first end of the support despite mispositioning of the sensor portion relative to the predetermined portion of the component.

In accordance with a preferred embodiment of that aspect of the present invention, the sensor is carried by a cylindrical adaptor which in turn is carried by an arm which is part of the support. The adaptor is mounted to the arm such that the sensor is permitted a limited amount of rotation about an axis perpendicular to the arm and a limited amount of rocking about a point on that axis. The effect of that mounting technique is to provide the sensor with a loose fit within the arm such that the sensor can engage the component to be inspected despite mispositioning between the second end of the support and the component and at the same time positively secure the sensor to the arm.

In accordance with another aspect of the present invention, the arm is connected to the elongated support by a swivel means which allows movement of the arm between a first position wherein the arm is substantially completely within the support and a second expanded position wherein the portion of the arm carrying the sensor extends laterally of the support such that the sensor is positioned for mating engagement with the component's predetermined portion. Actuator means are provided for controlling movement of the arm between the first and second positions. The actuator means comprise first gear means connected to the arm, second gear means matingly engaging the first gear means, and means for moving the second gear means to cause the arm to move between the first and second positions. The means for moving is associated with the first end of the support means so that control of the position of the arm is accomplished from a remote location.

Thus, when the arm is in the first position, within the support means, the support means may be pushed or pulled through any amount of piping or tubing without fear of damaging the sensor. When the support means reaches the location of the component to be inspected, the arm is moved into the second position such that the sensor may engage the component to be inspected.

In accordance with a further aspect of the present invention, an indicator is associated with the first end of the support means which provides a first indication when the sensor contacts the component to be inspected with a predetermined force and provides a second indication when the force is reduced upon the sensor's mating engagement with the predetermined portion of the component to be inspected.

In accordance with the method of the present invention, the mechanical delivery system is positioned with the housing adjacent to the component to be inspected. The arm is deployed and the entire delivery system is moved until the sensor comes into contact with the component to be inspected. The support means is then manipulated until the sensor matingly engages the predetermined portion of the component. In a preferred embodiment, after contact with the component is made, a delivery spring is used to increase the force on the sensor. The increase in force may be shown by a scale. The delivery system is then rotated until the sensor engages the component which will be apparent from a drop in force on the sensor shown by the scale. The force on the sensor may again be increased to insure proper contact before the inspection is performed.

Those and further features and characteristics of the present invention will be apparent from the following detailed description in which reference is made to the

BRIEF DESCRIPTION OF THE DRAWING

FIG. 3 is another cross-sectional view of the sensor housing taken along the line III—III;

FIG. 4 is detailed cross-sectional view of the arm which carries the ultrasonic transducers;

FIG. 4A is a view of the top surface of a portion of the arm of FIG. 3;

FIG. 5 is detailed view of an ultrasonic transducer, cylindrical adapter, and retaining clip.

DESCRIPTION OF THE PREFERRED EMBODIMENT

Figure 1:
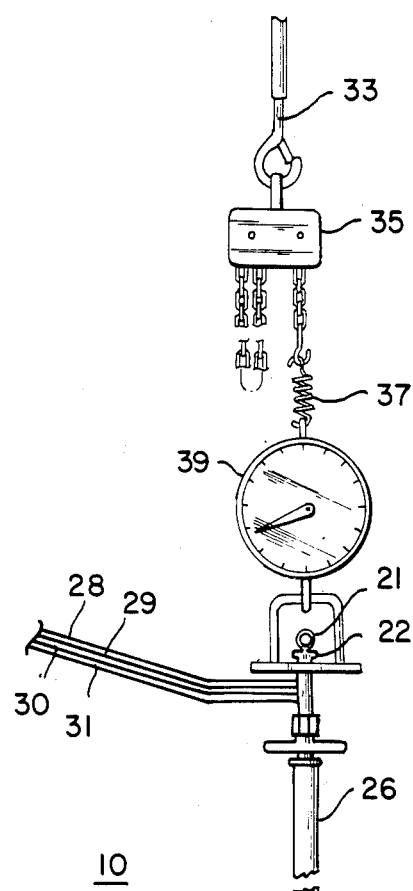
FIG. 1 illustrates the mechanical delivery system of the present invention.

FIG. 1 illustrates a mechanical delivery system 10 constructed according to the teachings of the present invention. The mechanical delivery system 10 has a sensor housing 12 located at its lowermost end. The housing 12 carries an arm 14 which is shown in its open position in FIG. 1. The arm 14 has a closed position, which is shown in FIG. 2.

The arm 14 carries a first contact-type ultrasonic sensor 16 and a second contact-type ultrasonic sensor 18. When the arm is in its open position as shown in FIG. 1, the sensors 16 and 18 extend laterally of the housing 12 and are capable of mating engagement with the component to be inspected. When the arm is in its closed position, as shown in FIG. 2, the sensors 16 and 18 are within the housing 12 and are thereby protected from damage while in transit to and from the inspection site.

Figure 2:
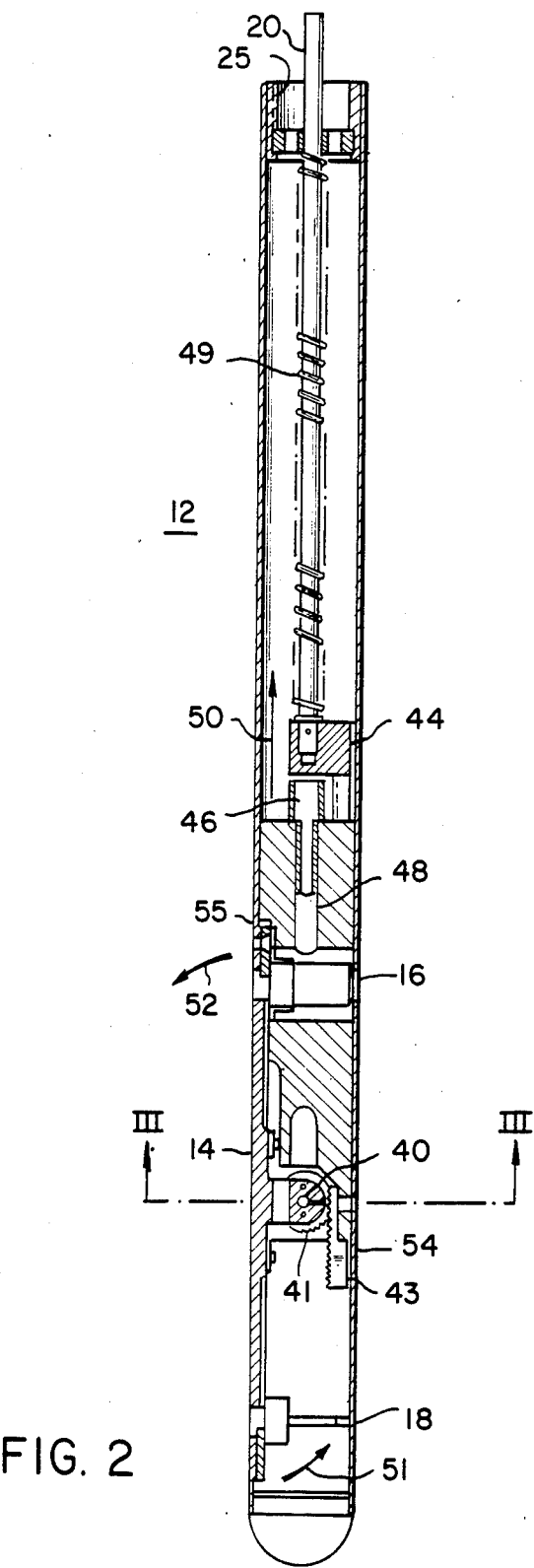
FIG. 2 is a cross-sectional view of the sensor housing of FIG. 1.

The arm 14 is operated by an actuator rod 20 shown in FIG. 2, which terminates in an eye nut 21 and threaded knob 22, both illustrated in FIG. 1. Because the distance between the eye nut 21 and the housing 12 may typically be forty feet, it is desirable to protect the actuator rod 20 with extension pipes 24. The first extension pipe 24 mates with threads 25, shown in FIG. 2, in the upper end of the housing 12. The extension pipe 24 at the uppermost end of the mechanical delivery system 10 is provided with an outer support 26. Electrical coaxial cables 28 and 29 from the transducer 16 and electrical coaxial cables 30 and 31 from the transducer 18 are also within, and protected by, the extension piping 24. The coaxial cables 28, 29, 30, and 31 are capable of being connected to ultrasonic instruments such as a MARK I provided by Sonic Corp.

The mechanical delivery system 10 is connected to a ceiling or crane hook 33 through a hoist 35, a delivery spring 37, and a scale 39. The eye nut 21, threaded knob 22, hoist 35, spring 37, and scale 39 are all used to precisely position the sensors 16 and 18 in a manner described hereinbelow in connection with FIG. 6.

Turning to FIGS. 2 and 3, cross-sectional views of the sensor housing 12 are shown. In FIG. 2, the arm 14 is shown in its closed position wherein it is parallel to and within the sensor housing 12. The arm 14 is connected to the sensor housing 12 by a connection pin 40 seen more clearly in FIG. 3. The arm 14 is responsive to two pinion gears 41 and 41' which in turn are responsive to two rack gears 43 and 43'. The rack, gears 43 and 43' terminate in a common enlarged upper end 44 which is connected to the actuator rod 20. The enlarged upper end 44 of the rack gears 43 and 43' is also connected to a pin 46 which engages a guide 48.

A biasing spring 49 is connected between the upper end of the housing 12 and the enlarged upper end 44 of the rack gears 43 and 43' with the control rod 20 running therethrough.

In operation, when the control rod 20 is pulled in the direction indicated by the arrow 50, the pin 46 and rack gears 43 and 43' move in the same direction. That movement causes the basing spring 49 to be compressed. That movement also causes the pinion gears 41 and 41' to rotate causing the arm 14 to swivel in the directions indicated by the arrows 51 and 52. The housing 12 has openings 54 and 55 to allow the arm to swivel into its open position which is perpendicular to the housing 12, as shown in FIG. 1.

When the force on the actuator rod 20 is released, the biasing spring 49 urges the rack gears 43 and 43' and the guide pin 46 back to their starting positions. That motion causes the arm 14 to swivel from the open position perpendicular to the housing 12 to its closed position as shown in FIG. 2. The guide pin 46 prevents stray movement of the rack gears 43 and 43' thus insuring positive engagement with pinion gears 41 and 41'. The second set of rack and pinion gears 43' and 41', respectively, have been added as a protective feature.

The first transducer 16 is mounted at a right angle, or 90°, with respect to the second transducer 18. That mounting arrangement is necessary for one embodiment of the present invention which will be described in detail hereinbelow in conjunction with FIG. 6.

The mounting of the first and second transducers 16 and 18, respectively, is an important feature of the present invention and will be described in detail in conjunction with FIGS. 4, 4A, and 5. It is to be understood that the following discussion of the mounting of the first transducer 16 is equally applicable to the second transducer 18.

In FIG. 4, a cross-sectional view of the arm 14 is shown. The arm 14 has a cylindrical opening 57 extending therethrough and a recessed portion 59. The cylindrical opening 57 and recessed portion 59 are seen from another view in FIG. 4A.

The transducer 16 is shown in detail in FIG. 5. An adapter 60 has an upper adapter portion 61 and a lower cylindrical adapter portion 62. The upper adapter portion 61 carries a transducer tongue 64 which houses an ultrasonic transmitter 81 and receiver 82. Two coaxial cables 28 and 29 extend from the transducer 16. The ultrasonic transducer may be of a type available from Ultran Laboratories, model WSP.

The lower adapter portion 62 is cylindrical and is sized to be received by the cylindrical opening 57 in the arm 14. The lower cylindrical adapter portion 62 also has a slot or notch 65. The slot 65 is defined by a bottom surface 66, a top surface 67, and a vertical wall 68.

When the lower cylindrical adapter portion 62 is inserted in the cylindrical opening 57, a flat retaining clip 69 is attached to the arm 14 by a screw (not shown), which extends through the clip 69 into mating threads 70 in the arm 14. The clip 69 is designed to be received by the recessed portion 59 of the arm 14 such that the clip 69 is flush with the top surface of the arm 14. When the retaining clip 69 is attached, a portion of the clip extends into the slop 65 of the lower cylindrical adapter portion 62. The dimensions of the cylindrical opening 57 in the arm 14, the lower cylindrical adapter portion 62, slot 65, and clip 69 are such that the transducer 16 is permitted limited rotation (until part of the vertical wall 68 of the slot 66 meets the end surface of the clip 69) about an axis perpendicular to the arm 14. The sensor 16 may also be permitted limited rocking (until the lower surface 66 or the upper surface 67 of the slot 65 meet the clip 69) about a point on the axis. That limited rotaiton and rocking is necessary because the arm 14 may not be exactly positioned for the transducer tongue 64 to be inserted into the component to be inspected. That limited rotation and rocking is also necessary in the event that the two components to be simultaneously inspected by the transducers 16 and 18 are not in the exact position anticipated.

The following chart summarizes the dimensions used in one embodiment to provide the sensors with the proper freedom to rotate about an axis perpendicular to the arm 14 and to rock about a point on that axis.

| Part | Dimension | Tolerance in Inches |
|---|---|---|
| lower cylindrical adapter 62 | .500" dia. (12.700 mm) | +.000 −.001 |
| cylindrical opening 57 | .501" dia. (12.725 mm) | +.001 −.000 |
| slot bottom surface 66 | .125" (3.175 mm) | ±.010 |
| extension of clip 69 into slot 66 | .117" (2.972 mm) | ±.001 |
| slot vertical wall 68 | .130" (3.302 mm) | +.005 −.000 |
| thickness of clip 69 | .124" (3.150 mm) | +.000 −.002 |

A mechanical delivery system 10 using the above dimensions would typically have a housing 12 having an outside diameter of 2.25" (57.15 mm) and a distance of about 7" (17.78 cm) between the transducers 16 and 18.

In addition to the attention that must be paid to the dimensions of the arm 14, lower cylindrical adapter portion 62, and the clip 69, the arm 14 is constructed of a hardened material and the adapter 60 of a softer material. Thus, the motion of a softer adapter material on a hardened material eliminates sticking and galling. The overall effect of the assembled arm 14 and transducer 16 is of a loose fit of the transducer 16 in the arm 14 but a fit which is nonetheless secure.

Figure 6:
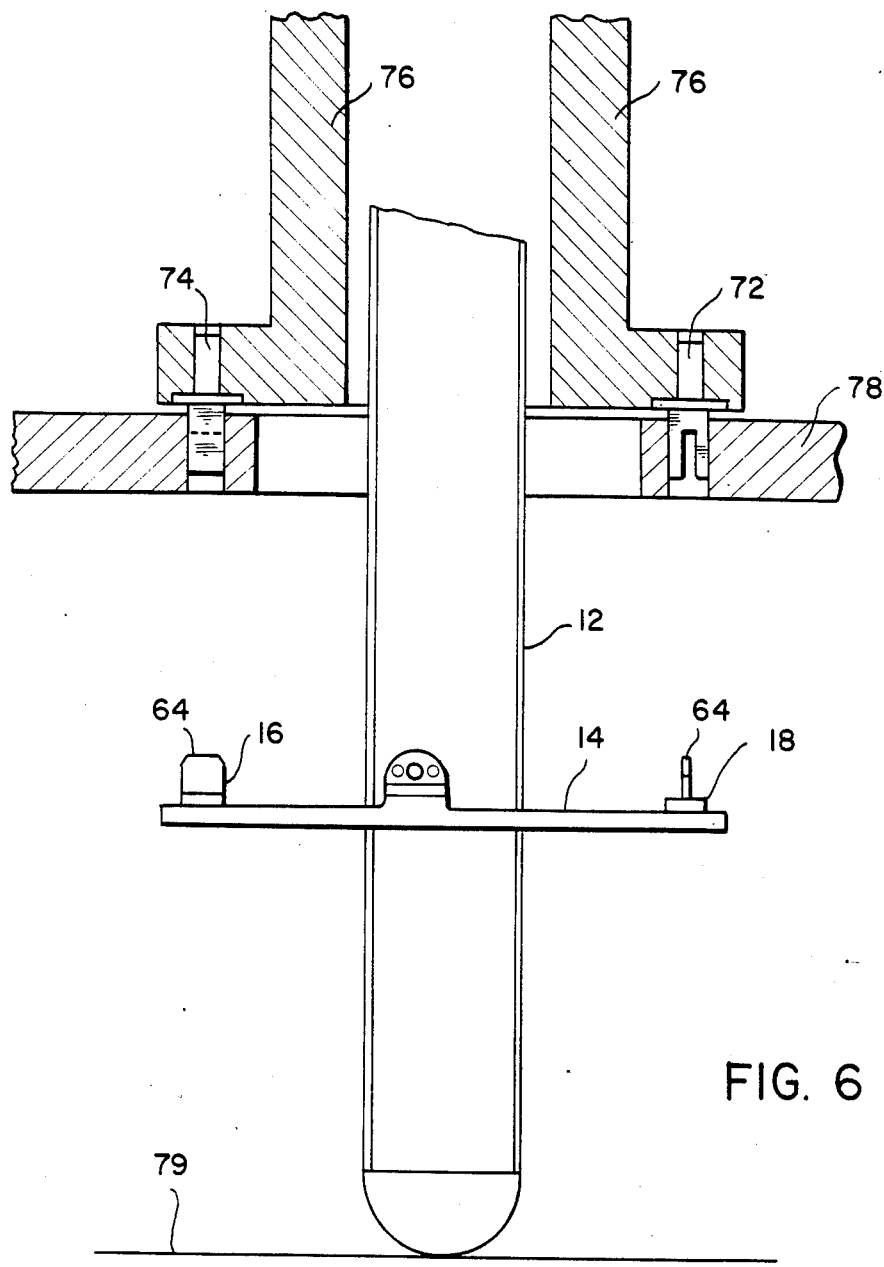
FIG. 6 illustrates the sensor housing of the mechanical delivery system of the present invention in operation in a particular environment.

The operation of the mechanical delivery system 10 shown in FIG. 1 will now be described in a particular environment in conjunction with FIG. 6. In FIG. 6, the mechanical delivery system 10 positions the ultrasonic sensors 16 and 18 for inspection of split pins 72 and 74. The split pins 72 and 74 are used to connect a guide tube 76, which is used to guide control rods (not shown), to an upper core plate 78. The ultrasonic sensor 16 and 18 inspect the split pins 72 and 74 for cracks or other signs of mechanical failure. The mechanical delivery system 10 enables examination of the split pins 72 and 74 while they are mounted in both the guide tube 76 and the upper core plate 78; the guide tube 76 and upper core plate 78 are mounted in the upper portion of a nuclear reactor. For ultrasonic examination, the upper reactor internals (not shown) are removed from the reactor vessel and seated on an upper internals storage stand in containment. The ultrasonic inspection of the split pins 72 and 74 is done remotely from a manipulator bridge in containment or unsuitable work platform with the split pins under water approximately forty feet below.

In that environment, the mechanical delivery system 10 must deliver the transducers 16 and 18 to the split pins 72 and 74 mounted in the guide tube 76 such that the operator can remotely examine the pins to assess whether the pins are structurally sound. The mechanical delivery system 10 must be able to remotely engage the tongue 64 of each transducer into the slot of the split pins 72 and 74. For example, that operation may involve inserting the tongue 64 having a nominal width of 0.094 inches (2.388 mm) into a slot of nominal width of 0.126 inches (3.200 mm) from a work platform forty feet above without the aid of a camera. The mechanical delivery system 10 must position the transducers 16 and 18 in the split pins such that the transducers can be made to translate along the length of the split pin slot as required by the operator performing the inspection. Further, the mechanical delivery system 10 must not damage the transducers 16 and 18 in delivering the transducers to the split pins, engaging the tongues 64 with the split pin slots, and removing the transducers even though the transducers 16 and 18 are relatively fragile. Finally, the mechanical delivery system 10 must be relatively simple to operate and capable of repetitive inspections. For example, in a typical four-day examination period, 60 split pins securing 30 guide tubes will be inspected. That inspection will include inserting the mechanical delivery system 10 into a guide tube, positioning the transducers 16 and 18 into the split pins, ultrasonically examining the split pins, and removing the mechanical delivery system 10 from the guide tube.

In FIG. 6, the housing 12 has been delivered to the floor 79 at the bottom of the cavity some forty feet below a work platform. When the bottom is reached, the eye nut 21 shown in FIG. 1, is pulled causing the swivel arm 14 to assume its open position as shown in FIG. 5. When the arm 14 has been fully opened, the threaded knob 22 is tightened to maintain the arm 14 in the open position.

The hoist 35, shown in FIG. 1, is used to lift the entire mechanical delivery system until the tongues 64 of the transducers 16 and 18 come in contact with the bottom of the upper core plate 78. Contact can be determined by noticing an increase in the reading of the scale 39 above the mechanical delivery system's hanging weight. Once contact has been established, the mechanical delivery system is raised until a load of five pounds is placed on the tongue of each of the transducers 16 and 18. The operator then rotates the mechanical delivery system from the work platform until the transducer tongues 64 "pop" into the split pin slots. That will be accomplished when the load on the scale 39 drops to the original hanging weight of the mechanical delivery system 10. Again using the hoist 35, the mechanical delivery system is raised until the tongue 64 of each of the ultrasonic sensors 16 and 18 experiences a load of five pounds. Once that has been accomplished, the split pins are ready to be ultrasonically inspected.

After inspection, the mechanical delivery system is lowered and the threaded knob 22 is loosened allowing the bias spring 49, shown in FIG. 2, to urge the arm 14 into its closed position. Once the arm 14 is in its closed position, the mechanical delivery system 10 can be removed from the guide tube 76. The process can be repeated until all of the split pins have been ultrasonically inspected.

The description of the present invention in conjunction with an environment wherein two split pins are ultrasonically inspected is intended merely as an example and not a limitation. It is anticipated with that principles of the present invention may be modified to suit a variety of environments. Such modifications may be made without departing from the scope and content of the present invention as defined by the following claims.

What is claimed is:

1. A mechanical delivery system for remotely positioning a sensor in mating engagement with a predetermined portion of a component to be inspected, comprising:

elongated support means for positioning a sensor, said elongate support means having a first end adapted for manipulation from a remote location and a second end having a housing;

a sensor having a sensor portion adapted for mating engagement with the predetermined portion of the component to be inspected; and mounting means for mounting said sensor to said support means at said second end of said support means, said mounting means movable between a first position and a second position, said mounting means positioning said sensor portion within said housing when in said first position and positioning said sensor portion extending laterally of said housing when in said second position to thereby enable said sensor portion to be placed in mating engagement with the predetermined portion of the component as a result of manipulation of said first end.

2. The mechanical delivery system of claim 1 wherein said sensor includes a ultrasonic transmitter and receiver.

3. The mechanical delivery system of claim 1, wherein said elongated support means defines a support axis along which said support means is adapted to be moved with respect to the component to be inspected by manipulation of said first end, and wherein said mounting means mounts said sensor such that said sensor is displaced laterally of said support axis.

4. The mechanical delivery system of claim 3, wherein said mounting means mounts said sensor for limited rotation of said sensor about a sensor axis defined by said sensor and limited rocking of said sensor about a point along said sensor axis.

5. The mechanical delivery system of claim 1 wherein said mounting means comprises an arm having an adapter carrying said sensor and mounted to said arm for limited movement with respect to said arm.

6. The mechanical delivery system of claim 5 wherein said adapter is cylindrical and wherein said arm has a cylindrical opening therein for receiving said adapter to permit limited rotation of said adapter within said cylindrical opening.

7. The mechanical delivery system of claim 6 wherein said adapter includes a notched portion and wherein said arm further includes a member rigidly connected to a portion of said arm and having a protruding portion extending into said notched portion, said protruding portion being of a smaller dimension than said notched portion to limit the degree of rotation of said adapter relative to said arm.

8. The mechanical delivery system of claim 7 wherein the diameter of said adapter is smaller than the diameter of said cylindrical opening to permit limited rocking of said sensor relative to said arm.

9. The mechanical delivery system of claim 7 wherein said member is a flat clip.

10. The mechanical delivery system of claim 9 wherein said arm includes a recessed portion such that said flat clip is flush with said arm's surface.

11. The mechanical delivery system of claim 1 in which said sensor comprises a first sensor having a first sensor portion adapted for engagement with a first predetermined portion of the component to be inspected and said mounting means comprises first mounting means for mounting said first sensor, said mechanical delivery system further including a second sensor having a second sensor portion adapted for mating engagement with a second predetermined portion of the component to be inspected, and including second mounting means for mounting said second sensor to said support means at said second end of the support means and displaced from said first sensor, said second mounting means mounting said second sensor so as to permit limited movement of said second sensor with respect to said second end to thereby enable said portion of said second sensor to be placed in mating engagement with said second predetermined portion of the component as a result of manipulation of the first end despite imprecise positioning of said second sensor portion relative to the component.

12. The mechanical delivery system of claim 1 wherein said housing receives therein said arm carrying said sensor.

13. The mechanical delivery system of claim 12 including swivel means connecting said arm to said housing for movement between said first position and said second position, said arm being substantially parallel to said housing when in said first position and extending laterally of said housing when in said second position, and actuator means for moving said arm between said first and second positions.

14. The mechanical delivery system of claim 13 wherein said housing is tubular and has openings therein such that said arm is inside said housing in said first position and portions of said arm are lateral of said housing in said second position.

15. The mechanical delivery system of claim 14 including a biasing spring biasing said arm toward said first position.

16. The mechanical delivery system of claim 13 wherein said actuator means includes first and second mating gears and an actuator rod having a first end adapted for manipulation from a remote location and a second end connected to said first gear, said second gear being connected to said arm.

17. The mechanical delivery system of claim 1 wherein said first end of the support means includes a delivery spring for supplying a force for aiding placement of said sensor portion in mating engagement with the component's predetermined portion.

18. The mechanical delivery system of claim 17 wherein said first end of said support means includes scale means responsive to said delivery spring for indicating the magnitude of said supplied force.

19. The mechanical delivery system of claim 1 wherein said sensor is mounted to said mounting means to permit limited movement with respect to said mounting means to thereby enable said sensor portion to be placed in mating engagement with the predetermined portion of the component as a result of manipulation of said first end of said elongated support means despite mispositioning of said sensor portion relative to said component.

20. A mechanical delivery system for remotely positioning a sensor in mating engagement with a predetermined portion of a component to be inspected, comprising:
elongated support means for positioning a sensor, said elongated support means having a first end adapted for manipulation from a remote location and a second end;
a sensor having a portion adapted for mating engagement with the predetermined portion of the component;
mounting means for mounting said sensor to said second end of said support means; and
indicator means associated with said first end of said support means for providing a first indication when said sensor contacts the component with a predetermined force and for providing a second indication when said force is reduced upon said sensor matingly engaging said predetermined portion.

21. The mechanical delivery system of claim 20 in which said predetermined portion of the component comprises a recess and said portion of said sensor is adapted to be received in said recess, and wherein said indicator means provides said second indication when said portion of said sensor is received in said recess.

22. The mechanical delivery system of claim 20 wherein said indicator means includes spring means.

23. The mechanical delivery system of claim 20 wherein said indicator means includes scale means.

24. The mechanical delivery system of claim 20 wherein the sensor includes an ultrasonic transmitter and receiver.

25. The mechanical delivery system of claim 20 wherein said second end of said support means includes an arm and wherein said mounting means includes a cylindrical adapter carrying said sensor and mounted to said arm for limited movement with respect to said arm.

26. The mechanical delivery system of claim 23 wherein said adapter includes a notched portion and wherein said mounting means further includes a member rigidly connected to said arm and having a protruding portion extending into said notched portion such that said sensor is permitted limited movement with respect to said arm thereby enabling said sensor portion to be placed in mating engagement with the component's predetermined portion despite mispositioning of said sensor portion relative to the component.

27. The mechanical delivery system of claim 26 wherein said member is a flat clip and said arm has a recessed portion such that said clip is flush with said arm's surface.

28. The mechanical delivery system of claim 20 wherein said elongated support means includes an actuator means, and wherein said second end of said support means includes a housing having an arm carrying said sensor, said arm being responsive to said actuator means.

29. The mechanical delivery system of claim 28 including swivel means for connecting said arm to said housing, said arm being responsive to said actuator means such that said arm is inside said housing in a first position and portions of said arm are lateral of said housing in a second position.

30. The mechanical delivery system of claim 29 including a biasing spring biasing said arm toward said first position.

31. The mechanical delivery system of claim 29 wherein said actuator means includes mating rack and pinion gears and an actuator rod having a first end adapted for manipulation from a remote location and a second end connected to said rack gear, said pinion gear connected to said arm.

32. A mechanical delivery system for remotely positioning a sensor in mating engagement with a predetermined portion of a component to be inspected, comprising:
elongated support means for positioning a sensor, said elongated support means having a first end adapted for manipulation from a remote location and a second end having a housing;
an arm carrying a sensor, said sensor having a sensor portion adapted for mating engagement with the component's predetermined portion;
swivel means for mounting said arm to said second end of said support means for movement between a first position wherein said arm is substantially completely within said support means such that said sensor portion is received within said housing, and a second expanded position wherein the portion of said arm carrying said sensor extends laterally of said support means such that said sensor portion is positioned outside said housing for mating engagement with the predetermined portion of the component; and
actuator means for moving said arm between said first and second positions, said actuator means including first gear means connected to said arm, scond gear means matingly engaging said first gear means, and means associated with said first end of said support means for moving said second gear means to cause said arm to move between said first and second positions.

33. The mechanical delivery system of claim 32 wherein said actuator means for moving comprises an actuator rod having a first end adapted for manipulation from a remote position and a second end connected to said second gear means.

34. The mechanical delivery system of claim 32 wherein said mating first and second gear means includes rack and pinion gears.

35. The mechanical delivery system of claim 32 wherein said first end of said support means includes a delivery spring for supplying a force for aiding placement of said sensor portion in mating engagement with the component's predetermined portion and includes scale means responsive to said delivery spring for indicating the magnitude of said supplied force.

36. A method of remotely positioning a sensor in mating engagement with a predetermined portion of a component to be inspected, comprising the steps of:
positioning the lower end of an elongated support adjacent the component to be inspected;
deploying an arm carrying the sensor from the lower end of said elongated support;
bringing the sensor into contact with the component to be inspected;
manipulating the elongated support until the sensor matingly engages the component's predetermined portion; and
providing a first indication when said sensor contacts the component with a predetermined force and providing a second indication when said force is reduced upon said sensor matingly engaging said predetermined portion.

37. The method of claim 36 wherein said manipulation step includes applying a force between said sensor and the component to be inspected in a manner such that said force is decreased automatically when said sensor matingly engages the component's predetermined position.

38. The method of claim 37, in which the predetermined portion of the component comprises a recess in the component and said sensor is adapted to be received in the recess, and wherein said step of manipulation comprises moving said support until a decrease in said force is detected.

39. The method of claim 37 wherein said force is kept below the value of a force necessary to damage said sensor.

40. The method of claim 37 including the step of measuring said force between said sensor and the component to be inspected.

41. The method of claim 36 including the step of increasing the force on said sensor after said sensor matingly engages the component's predetermined portion.

42. The method of claim 36 wherein said manipulating step includes rotating said elongated support.

43. A mechanical delivery system for remotely positioning a sensor in mating engagement with a predetermined portion of a component to be inspected, comprising:

elongated support means for positioning a sensor, said elongated support means having a first end adapted for manipulation from a remote location and a second end, said second end of said support means including an arm having an opening therein;

a sensor having a sensor portion adapted for mating engagement with the predetermined portion of the component to be inspect;

an adapter having a notched portion, said adapter carrying said sensor and mounted to said arm for limited movement with respect to said arm, said opening within said arm receiving said adapter to permit limited rotation of said adapter within said opening; and mounting means for mounting said sensor to said arm at said second end of said support means such that said sensor is permitted limited movement with respect to said arm to thereby enable said sensor portion to be placed in mating engagement with the predetermined portion of the component as a result of manipulation of said first end despite mispositioning of said sensor portion relative to the component, said mounting means including a member rigidly connected to said arm and having a protruding portion extending into said notched portion of said adapter, said protruding portion being of a smaller dimension that said notched portion to limit the degree of rotation of said adapter relative to said arm.

44. A method of remotely positioning a sensor in mating engagement with a predetermined portion of a component to be inspected, comprising the steps of:

positioning the lower end of an elongated support adjacent the component to be inspected;

deploying an arm carrying the sensor from the lower end of said elongated support;

bringing the sensor into contact with the component to be inspected; and manipulating the elongated support until the sensor matingly engages the component's predetermined portion, said manipulating step including applying a force between said sensor and the component to be inspected in a manner such that said force is decreased automatically when said sensor matingly engages the component's predetermined position.

* * * * *